(12) United States Patent
Vandersall et al.

(10) Patent No.: US 7,711,491 B2
(45) Date of Patent: May 4, 2010

(54) COMPUTATIONAL METHOD AND SYSTEM FOR MODELING, ANALYZING, AND OPTIMIZING DNA AMPLIFICATION AND SYNTHESIS

(75) Inventors: Jennifer A. Vandersall, Livermore, CA (US); Shea N. Gardner, San Leandro, CA (US); David S. Clague, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 272 days.

(21) Appl. No.: 10/840,779

(22) Filed: May 5, 2004

(65) Prior Publication Data
US 2004/0224345 A1 Nov. 11, 2004

Related U.S. Application Data

(60) Provisional application No. 60/468,313, filed on May 5, 2003, provisional application No. 60/506,137, filed on Sep. 25, 2003.

(51) Int. Cl.
*G01N 33/48* (2006.01)
*C12Q 1/68* (2006.01)
*C12N 15/11* (2006.01)

(52) U.S. Cl. .............................. 702/19; 702/20; 435/6; 536/23.1; 536/24.1

(58) Field of Classification Search ....................... None
See application file for complete search history.

*Primary Examiner*—Shubo (Joe) Zhou
(74) *Attorney, Agent, or Firm*—James S. Tak

(57) ABSTRACT

A computational method and computer-based system of modeling DNA synthesis for the design and interpretation of PCR amplification, parallel DNA synthesis, and microarray chip analysis. The method and system include modules that address the bioinformatics, kinetics, and thermodynamics of DNA amplification and synthesis. Specifically, the steps of DNA selection, as well as the kinetics and thermodynamics of DNA hybridization and extensions, are addressed, which enable the optimization of the processing and the prediction of the products as a function of DNA sequence, mixing protocol, time, temperature and concentration of species.

9 Claims, 5 Drawing Sheets

COMPUTATIONAL METHOD AND SYSTEM FOR MODELING, ANALYZING, AND OPTIMIZING DNA AMPLIFICATION AND SYNTHESIS

I. CLAIM OF PRIORITY IN PROVISIONAL APPLICATION

This application claims priority in provisional application filed on May 5, 2003, entitled "Computational Methods to Analyze and Optimize DNA Amplification and Synthesis" Ser. No. 60/468,313, and provisional application filed on Sep. 25, 2003, also entitled "Computational Methods to Analyze and Optimize DNA Amplification and Synthesis" Ser. No. 60/506,137, both by Jennifer A. Young et al.

The United States Government has rights in this invention pursuant to Contract No. W-7405-ENG-48 between the United States Department of Energy and the University of California for the operation of Lawrence Livermore National Laboratory.

II. FIELD OF THE INVENTION

The present invention relates to computational modeling methods and computer-based modeling tools. More particularly, the present invention relates to a computational method and system for modeling parallel DNA synthesis and the complete PCR amplification process by integrating the bioinformatic, thermodynamic, and kinetic aspects of PCR.

III. BACKGROUND OF THE INVENTION

PCR (i.e. Polymerase Chain Reaction) technology is fundamental to modern biology and is considered among the most important scientific developments for the analysis of biological sequence data. Used in virtually every laboratory conducting molecular, cellular, genetic, ecologic, forensic, or medical research, among others, PCR generally involves the amplification of DNA by subjecting a DNA fragment to a series of heating and cooling cycles, including denaturing the DNA by heating, annealing oligonucleotide primers to complementary bases during cooling, and heating with polymerase for DNA extension and synthesis.

Despite its ubiquity, the precise details about the effects of DNA sequence and reaction/processing conditions on the PCR product is currently lacking, as well as the ability to predict all products of PCR amplification as a function of DNA sequence and reaction conditions. In particular, the effects of time, temperature, ion concentration, complex sequence mixtures containing primer perfect matches and/or sequence mismatches, and the locations of mismatches within primer sequences (3',5', or central) are not well understood, as well as what products are amplified when complex sequence mixtures are present containing multiple, closely related targets and multiple primers which may hybridize with sequence mismatches. A better understanding of these issues and the ability to predict all PCR products can improve the design, interpretation, and detailed optimization of PCR reactions.

Various developments in computational PCR reaction design, such as the development of DNA melting programs, have demonstrated the importance of calculations in PCR analysis. Such efforts, however, do not adequately address the underlying physics and biology of the problem; only examine isolated aspects of the systems; and do not follow all significant reaction pathways which arise during the process. Specifically, while various software programs are available for PCR reaction design they are generally limited to selecting a "best" primer or, examining how reaction conditions effect the desired reactions during only the first thermocycle. For example, commercially available bioinfomatics programs, such as Primer3, PRIMO, Primer Design, and Oligonucleotide, return a list of best primers for a specific target based on sequence similarities, primer length, and melting temperatures, using simple GC content equations or Nearest Neighbor parameters, described in "Thermodynamics and NMR of internal G.T mismatches in DNA" by Allawi, H T and Santalucia, J, Jr., Biochem 36, 10581-10594 (1997), incorporated by reference herein. And more recent programs, such as Visual OMP, provide the ability to predict the concentration of hybridized species for only the first round of PCR for a given set of reaction conditions. However, they do not include, for example, modeling of extension, replication, or multiple thermocycles; do not run in parallel which hinders the modeling of complex mixtures and limits the complexity of mixtures that can be modeled; assume that all reactions proceed to equilibrium without considering non-equilibrium conditions; and do not consider the effects of competitive contaminants.

As suggested above, current practices estimate PCR products based solely on thermodynamics. However, in order to gain insight into the dynamics of the process and to optimize cycle processing conditions, there is a need to employ reaction kinetics. Traditionally, researchers have described the reaction kinetics using deterministic methods. While these approaches are valuable, it is well known that biochemical processes are stochastic in nature. This is suggested in "Computational and Experimental Analysis of DNA Shuffling" by Maheshri, N and Schaffer, D V (2003), Proc Natl Acad Sci USA 100, 3071-3076, where probabilistic methods were applied to modify rates of reaction to describe the DNA shuffling process. However, the probabilities of competitive events to describe the rates of stochastic events are not considered.

There is therefore a need for a complete and integrated computational model and methodology that enables the prediction of both the sequences and the concentrations of all species of hybridized and single strand sequences that are amplified during PCR. And in particular, there is a need for a computational method and computer-based system that not only models all relevant parts of the PCR process under investigation and the resulting reaction pathways, but also integrates the results by using the output of one modeling calculation as input into a subsequent modeling calculation. Furthermore, a need exists to derive probabilities of competitive events to describe the rates of stochastic events to provide a generalized framework that can be applied to describe the time-evolution of a host of biochemical processes. In this manner, a full spectrum of PCR products can be predicted after multiple thermocycles.

IV. SUMMARY OF THE INVENTION

One aspect of the present invention includes a method in a computer system for computationally modeling parallel DNA synthesis using a polymerase enzyme, the method comprising: in a bioinformatics module: receiving a desired full-length DNA sequence and a length of starting oligos; using said desired full-length DNA sequence and a first pre-defined set of sequence-based rules to determine optimal starting oligos and well allocations of said optimal starting oligos capable of reducing the production of undesired product; and using a second pre-defined set of sequence-based rules to determine an optimal protocol for mixing the products of a first thermocycle into wells for subsequent thermocycles; in a thermodynamics module: using said optimal starting oligos and well allocations determined in said bioinformatics module to track all significant reaction pathways that arise during each thermocycle and hybridization in terms of equilibrium thermodynamics by determining, for a given mix of DNA, the probability of hybridization for all possible combinations of oligos as determined by the free energies of interaction, wherein the concentrations of single and hybridized sequences in each well are determined as a function of processing conditions; extending all hybridized strands which can be biologically extended by the polymerase; and using all sequences and concentrations in a thermocycle as input for a subsequent thermocycle; in a kinetic module, using said optimal starting oligos and well allocations determined in said bioinformatics module to track temporal and spatial evolution of hybridization and polymerization for all of said significant reaction pathways that arise during thermocycling and hybridization by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and predicting synthesis products based on outputs of said thermodynamic module and said kinetic module.

Another aspect of the present invention includes a computer system for computationally modeling parallel DNA synthesis using a polymerase enzyme, the computer system comprising: a bioinformatic module adapted to receive a desired full-length DNA sequence and a length of starting oligos; use said desired full-length DNA sequence and a first pre-defined set of sequence-based rules to determine optimal starting oligos and well allocations of said optimal starting oligos capable of reducing the production of undesired product; and use a second pre-defined set of sequence-based rules to determine an optimal protocol for mixing the products of a first thermocycle into wells for subsequent thermocycles; a thermodynamics module adapted to use said optimal starting oligos and well allocations determined in said bioinformatics module to track all significant reaction pathways that arise during each thermocycle and hybridization in terms of equilibrium thermodynamics by determining, for a given mix of DNA, the probability of hybridization for all possible combinations of oligos as determined by the free energies of interaction, wherein the concentrations of single and hybridized sequences in each well are determined as a function of processing conditions; extended all hybridized strands which can be biologically extended by the polymerase; and use all sequences and concentrations in a thermocycle as input for a subsequent thermocycle; a kinetic module adapted to use said optimal starting oligos and well allocations determined in said bioinformatics module to track temporal and spatial evolution of hybridization and polymerization for all of said significant reaction pathways that arise during thermocycling and hybridization by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and an output module for predicting synthesis products based on outputs of said thermodynamic module and said kinetic module.

Another aspect of the present invention includes a computer program product comprising: a computer usable medium having computer readable program code embodied therein for causing the computational modeling of PCR processes, the computer readable program code comprising: computer readable program code means for receiving a desired full-length DNA sequence and a length of starting oligos; using said desired full-length DNA sequence and a first pre-defined set of sequence-based rules to determine optimal starting oligos and well allocations of said optimal starting oligos capable of reducing the production of undesired product; and using a second pre-defined set of sequence-based rules to determine an optimal protocol for mixing the products of a first thermocycle into wells for subsequent thermocycles; computer readable program code means for using said optimal starting oligos and well allocations determined in said bioinformatics module to track all significant reaction pathways that arise during each thermocycle and hybridization in terms of equilibrium thermodynamics by determining, for a given mix of DNA, the probability of hybridization for all possible combinations of oligos as determined by the free energies of interaction, wherein the concentrations of single and hybridized sequences in each well are determined as a function of processing conditions; extending all hybridized strands which can be biologically extended by the polymerase; and using all sequences and concentrations in a thermocycle as input for a subsequent thermocycle; computer readable program code means for using said optimal starting oligos and well allocations determined in said bioinformatics module to track temporal and spatial evolution of hybridization and polymerization for all of said significant reaction pathways that arise during thermocycling and hybridization by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and computer readable program code means for predicting synthesis products based on outputs of said thermodynamic module and said kinetic module.

Another aspect of the present invention includes a method in a computer system for computationally modeling PCR processes, the method comprising: in a bioinformatics module: generating candidate primers and suggesting potential starting sequence mixtures with their associated concentrations; in a thermodynamics module: using said starting sequence mixtures and primers specified in said bioinformatics module as input to track all significant reaction pathways that arise during each thermocycle and hybridization in terms of equilibrium thermodynamics by determining, for a given mix of DNA/RNA the probability of DNA hybridization for all possible combinations of oligos as determined by the free energies of interaction, wherein the concentrations of single and hybridized sequences in each well are determined as a function of processing conditions; extending hybridized strands which can be biologically extended by the polymerase; and (c) using as input all sequences and concentrations for a subsequent thermocycle; in a kinetic module: using said primers and starting sequence mixtures determined in said bioinformatics module to track temporal and spatial evolution of DNA hybridization and polymerization for all of said significant reaction pathways that arise during PCR and hybridization by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and predicting PCR products based on outputs of said thermodynamic module and said kinetic module.

Another aspect of the present invention includes a computer system for computationally modeling PCR processes, the computer system comprising: a bioinformatics module adapted to generate candidate primers and suggest potential starting sequence mixtures with their associated concentrations; a thermodynamics module adapted to use said starting sequence mixtures and primers specified in said bioinformatics module as input to track all significant reaction pathways that arise during each thermocycle and hybridization in terms of equilibrium thermodynamics by determining, for a given mix of DNA/RNA the probability of DNA hybridization for all possible combinations of oligos as determined by the free energies of interaction, wherein the concentrations of single and hybridized sequences in each well are determined as a function of processing conditions; extend hybridized strands which can be biologically extended by the polymerase; and (c) use as input all sequences and concentrations for a subsequent thermocycle; a kinetic module adapted to use said primers and starting sequence mixtures determined in said bioinformatics module to track temporal and spatial evolution of DNA hybridization and polymerization for all of said significant reaction pathways that arise during PCR and hybridization by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and an output module for predicting PCR products based on outputs of said thermodynamic module and said kinetic module.

Another aspect of the present invention includes a computer program product comprising: computer readable program code means for generating candidate primers and suggesting potential starting sequence mixtures with their associated concentrations; computer readable program code means for using said starting sequence mixtures and primers specified in said bioinformatics module as input to track all significant reaction pathways that arise during each thermocycle and hybridization in terms of equilibrium thermodynamics by determining, for a given mix of DNA/RNA the probability of DNA hybridization for all possible combinations of oligos as determined by the free energies of interaction, wherein the concentrations of single and hybridized sequences in each well are determined as a function of processing conditions; extending hybridized strands which can be biologically extended by the polymerase; and (c) using as input all sequences and concentrations for a subsequent thermocycle; computer readable program code means for using said primers and starting sequence mixtures determined in said bioinformatics module to track temporal and spatial evolution of DNA hybridization and polymerization for all of said significant reaction pathways that arise during PCR and hybridization by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and computer readable program code means for predicting PCR products based on outputs of said thermodynamic module and said kinetic module.

V. BRIEF DESCRIPTION OF THE DRAWINGS

The accompanying drawings, which are incorporated into and form a part of the disclosure, are as follows.

VI. DETAILED DESCRIPTION OF THE PRESENT INVENTION

Figure 1:
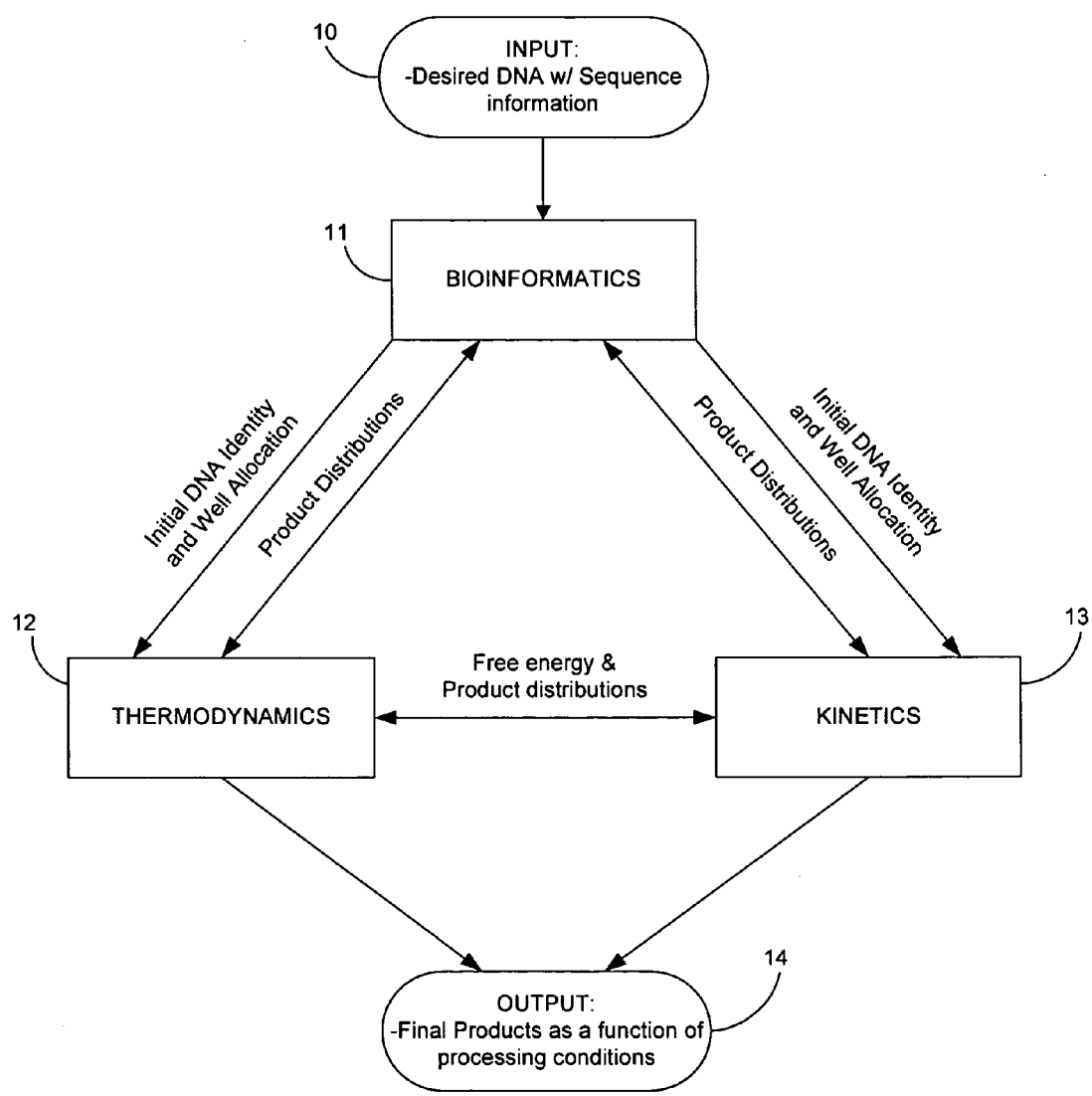
FIG. 1 is an overview flow diagram of the computational modeling method and system of the present invention.

The present invention is generally directed to a computational method and system utilizing computational tools (e.g. a linked suite of programs) to computationally model the complete PCR process of hybridization and polymerization, and optimize the production/amplification and prediction of PCR products, i.e. DNA, as a function of target DNA sequence, primers/probes, and reaction/processing conditions, (hereinafter "virtual PCR"). The reaction/processing conditions considered include, for example, choice of starting oligos, well allocation of the starting oligos, mixing protocol, time, temperature, ion concentration, complex sequence mixtures containing primer perfect matches and/or sequence mismatches, and the locations of mismatches within primer sequences (3',5', or central).

In particular, the computational method and system uses interlinked bioinformatics, thermodynamics, and kinetics modules (FIGS. 2-5) to model the kinetics and thermodynamics of probe/DNA annealing, along with the kinetics of polymerase association and extension for all significant reaction pathways that arise during PCR. The modules perform iterative simulations of polymerization kinetics and extension for multiple PCR cycles, using the products of one PCR thermocycle as input for the next cycle (such iterative process having a "pyramid" organization), to track the distribution of reaction products over time. Intermediate products can cross-react among themselves, thus amplifying undesired segments of DNA. Because each PCR thermocycle causes an exponential escalation in the number of possible reaction pathways, the use of parallel processing algorithms on parallel computer systems is preferred to process these complex reactions. In this regard, it is appreciated that each module may be provided as a computer readable and executable code in, for example, a linked suite of software programs, or as a component, e.g. IC, of a computer system designed to perform virtual PCR, as conventionally known in the arts of computer hardware and software.

It is appreciated that many of the parameters utilized in the bioinformatics, thermodynamic, and kinetic modules of the present invention are known in the art of DNA amplification and provided in the associated literature, such as: empirically-based free energy parameters for base pair annealing, rate constants of polymerase extension, and diffusion rates. In particular, these parameters are provided by the following references which are incorporated by reference herein, including (1) SantaLucia, J, Jr. (1998), "A unified view of polymer, dumbbell, and oligonucleotide DNA nearest-neighbor thermodynamics" Proc. Natl. Acad Aci, USA 95, 1460-1465; (2) Allawi, H T and Santalucia, J, Jr. (1997), "Thermodynamics and NMR of internal G. T mismatches in DNA" Biochem 36, 10581-10594; (3) Wetmur J G. (1991), "DNA probes: applications of the principles of nucleic acid hybridization" Crit Rev Biochem Mol Biol 26, 227-59; (4) McAdams, H H and Arcsine, A. (1997), "Stochastic mechanisms in gene expression" Proc Natl Acad Sci 94, 814-819; (5) Maheshri, N and Schaffer, D V. (2003), "Computational and Experimental Analysis of DNA Shuffling" Proc Natl Acad Sci USA 100, 3071-3076; (6) Gillespie, D. (1976). "*A Gen-* eral Method for Numerically Simulating the Stochastic Time Evolution of Coupled Chemical Reactions" J Comp Physics 22, 403-434; (7) Gibson, M A and Bruck, J. (2000), "Efficient Exact Stochastic Simulation of Chemical Systems with Many Species and Many Channels" J Phys Chem 104, 1876-1889, and (8) Gillespie, D and Petzold L R. (2003), "Improved Leap-Size Selection for Accelerated Stochastic Simulation" J Chem Phys 119, 8229-8234. Since many of these parameters are a function of DNA sequence identities and their concentrations, as well as temperature and ion concentrations, the present invention enables the detailed study of the effects that these parameters have on PCR products that is experimentally infeasible. In particular, the present invention operates to numerically solve the master stochastic kinetic equation described in "A General Method for Numerically Simulating the Stochastic Time Evolution of Coupled Chemical Reactions" by Gillespie, Journal of Comparative Physics 22, 403-434 (1976), incorporated by reference herein, and derive probabilities of competitive events to describe the rates of stochastic events. This approach provides a generalized framework that can be applied to describe the time-evolution of a host of biochemical processes.

Turning now to the drawings, FIG. 1 shows a flow chart of the overall organization of the method and system of the present invention, and the exchange of data between the main modules, including a bioinformatics module, a thermodynamics of DNA hybridization and extension module ("thermodynamics module"), and a kinetics of DNA hybridization and extension module ("kinetics module"). These component modules are shown in detail in FIGS. 2-5, and are interdependent in that the output of one module may directly serve as the input of another module. Depending on the application of interest, one or all of these tools may be utilized.

As shown in FIG. 1, a desired/target DNA sequence information is provided as input at 10 to the bioinformatics module 11. The bioinformatics module is linked to both the thermodynamics module 12 and the kinetic module 13. The bioinformatics module 11 determines the optimal starting oligos and well allocations for parallel synthesis, as well as optimal protocol for mixing wells within the pyramid organization, i.e. the number of layers of mixing required to obtain the desired DNA, and a determination of which wells to mix within each layer. These determinations are shared with both the thermodynamic 12 and kinetic 13 modules for use in their respective functions. And the goal of the thermodynamics module 12 is to predict all possible equilibrium DNA products as a function of sequence, temperature, concentration and number of thermocycles. Output from the thermodynamics module, i.e. product distributions, is used by the kinetics module 13 and the bioinformatics module 11. And the goal of the kinetic module 13 is to predict the non-equilibrium time evolution of DNA products as a function of temperature. Output from the kinetic module, i.e. free energy and product distributions, is used by the thermodynamics module 12 and the bioinformatics module 11. It is notable that the output of product distribution determination from both the thermodynamic and kinetic modules and sent to the bioinformatics module is utilized for the selection of optimal starting oligos and well allocations for the next PCR thermocycle. And as shown at 14, the thermodynamics 12 and kinetic modules 13 produce as output, detailed information on the final products as a function of processing conditions. The following will discuss each module in detail.

Bioinformatics Module

Generally, the bioinformatics module analyzes the desired/target DNA product to minimize annealing errors and the use of difficult sequences, e.g. GGG, as well as to eliminate or determine the sequence of unwanted oligomers. In particular, the bioinformatics module uses sequence identity of the desired/target DNA to determine optimal starting fragments, their allocation in wells, and subsequent mixing for parallel synthesis. Furthermore, a pre-defined (e.g. user-defined) set of sequence-based rules is applied to the target DNA, which then outputs the starting DNA oligos (i.e. fragments) and well allocations that will minimize or eliminate the production of undesired product. The pre-defined sequence-based rules that are considered in this module of the software include the length of starting fragments, melting temperatures, self complementarity of fragments (explain), incorrect but perfectly matching hybridizations, mismatched fragments that nevertheless have high melting temperatures, fragment sequences that are difficult to synthesize (e.g. GGG), and overlap between wells. Similar rules are used to determine the optimal manner/protocol of mixing the products of the first PCR cycle into wells for subsequent PCR cycles.

Figure 2:
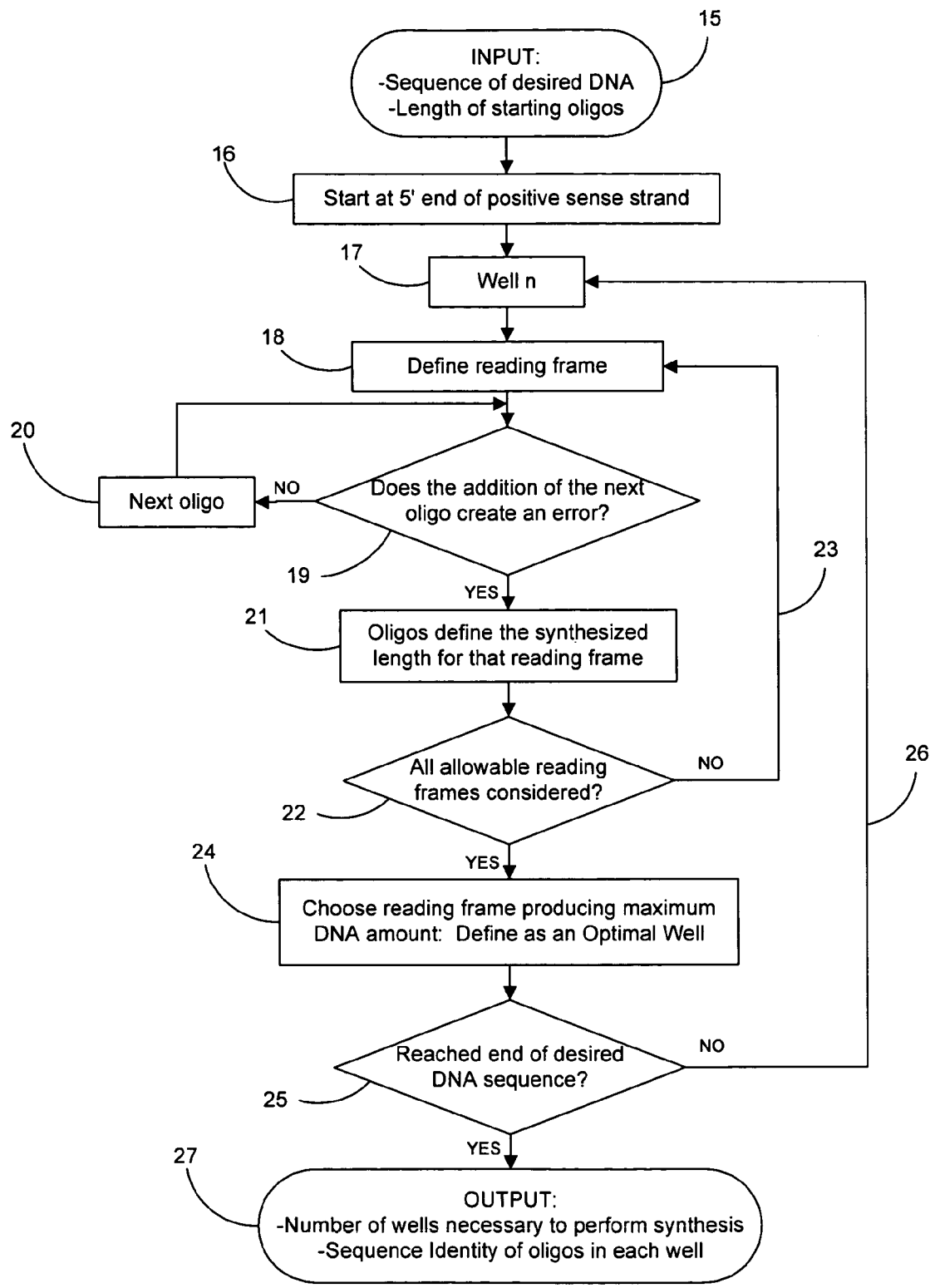
FIG. 2 is a flow diagram of an exemplary first bioinformatics module of the present invention.

FIG. 2 shows a flow diagram of a first bioinformatics module having as inputs: the sequence of desired DNA, and the length of starting oligos, indicated at box 15. At box 16 the module begins its analysis by starting at the 5' end of the positive sense strand of the desired/target DNA sequence. From that end, the determination of optimal wells begins at box 17. In particular, for each well n, reading frames are defined at 18 to begin an iterative process for determining optimal wells, i.e. selecting a reading frame for each well to maximize the number of n-mers/well, while minimizing the total number of wells.

At step 19, a determination is made whether the addition of the next oligo in the sequence creates an error. An error is considered to be, for example, perfect but undesired hybridizations, Tm's (melting temperatures) of undesired hybridizations are too close to those of desired hybridizations, large disparity in Tm's of desired hybridizations within a well, or oligo contains a sequence pattern that is difficult to create in chemical synthesis. If there is no error, the error determination is repeated with the next oligo in the sequence, as indicated at 20. If an error is created, the current reading frame is associated with the synthesized length up to that point. And as indicated at 23 the method returns to box 18 to repeat the process of defining a reading frame if all allowable reading frames have not been considered, as determined at 22. Allowable reading frames are defined by the minimum and maximum overlaps between wells, with the overlap chosen to be large enough to accurately hybridize wells in the next cycle.

When the loop for defining reading frames is completed, the reading frame which produces the maximum amount of DNA is selected and defined as an optimal well at box 24. Optimal well determination and selection is repeated as indicated by arrow 26 if the end of the desired/target DNA sequence has not been reached, as determined at 25. If the end of the sequence has been reached, and all optimal wells are established, step 27 provides the outputs of the bioinformatics module I to the thermodynamics module and kinetic module, where the output includes: the number of wells necessary to perform synthesis, and the sequence identity of oligos in each well.

Figure 3:
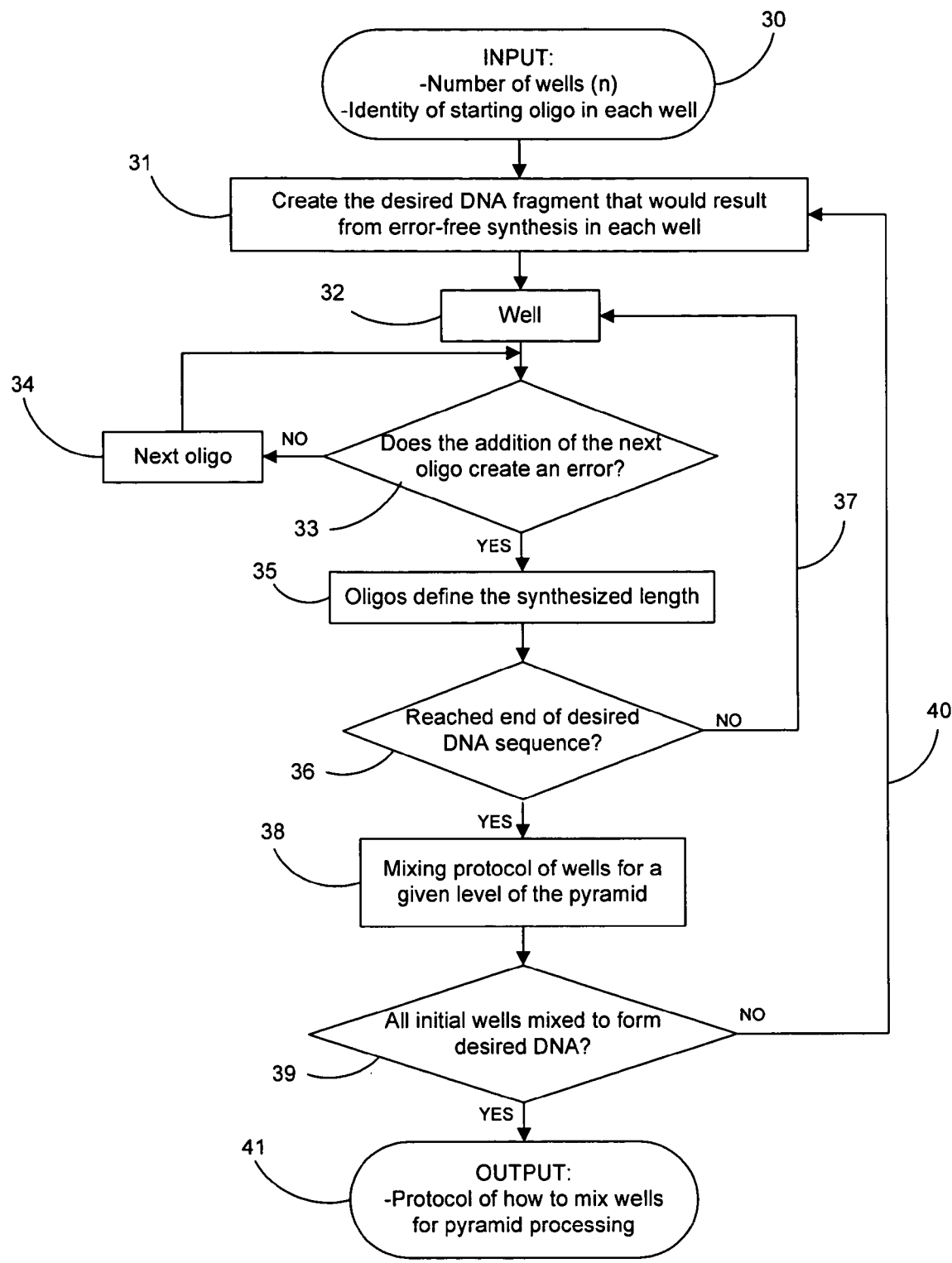
FIG. 3 is a flow diagram of an exemplary second bioinformatics module of the present invention.

FIG. 3 shows a flow diagram of a second bioinformatics module, having as inputs the number of wells (n), and the identity of starting oligos in each well, indicated at 30 and both obtained from the first Bioinformatics module. At box 31 the desired DNA fragment is created that would result from error-free synthesis in each well. Beginning at step 32, an error determination is made for each well until the end of the desired DNA sequence is reached. First, at step 33, a determination is made whether the addition of the desired oligomer contained in the next well creates an error. Here also, an error may include perfect but undesired hybridizations, Tm's of undesired hybridizations are too close to those of desired hybridizations, large disparity in Tm's of desired hybridizations within a well. If no error is found, the error determination is repeated for the same well, as indicated at box 34. If an error is found, the addition of the desired oligomer is used to define the synthesized length. This error determination is repeated for each well, as indicated by arrow 37 if the end of the desired DNA sequence has not been reached, as determined at 36. If the end of the desired DNA sequence has been reached, then a mixing protocol of wells is provided for a given level of the pyramid at step 38. This is repeated until all initial wells are mixed to form desired DNA, as indicated by return arrow 40, based on a determination at step 39. The output from this module, indicated at 41, is the protocol of how to mix wells for pyramid processing, and is provided to the thermodynamics and kinetic modules.

Thermodynamics Module

Generally, the thermodynamics module examines all of the significant reaction pathways that arise during PCR and hybridization in terms of equilibrium thermodynamics. Specifically, given a mix of DNA, the thermodynamics module examines the probability of DNA hybridization for all possible combinations of fragments as determined by the free energies of interaction. For reaction pathways which are characterized by a 5' overhang, the software simulates DNA extension. The effects of mismatches at the 3' end are accounted for in this simulation. These newly synthesized DNA fragments are then used as input to the next thermocycle. The thermodynamic module is capable of tracking all the possible reaction pathways resulting from each thermocycle, thus yielding information about the concentration and sequence identity of the product as a function of temperature, thermocycle and concentration, as well as the fragment identity and mixture determined by the bioinformatics module. The parameters for this module are nearest neighbor parameters for DNA melting and the probabilities of polymerase extensions as a function of base pair mismatches, which are available in the literature and known in the art of DNA amplification.

Figure 4:
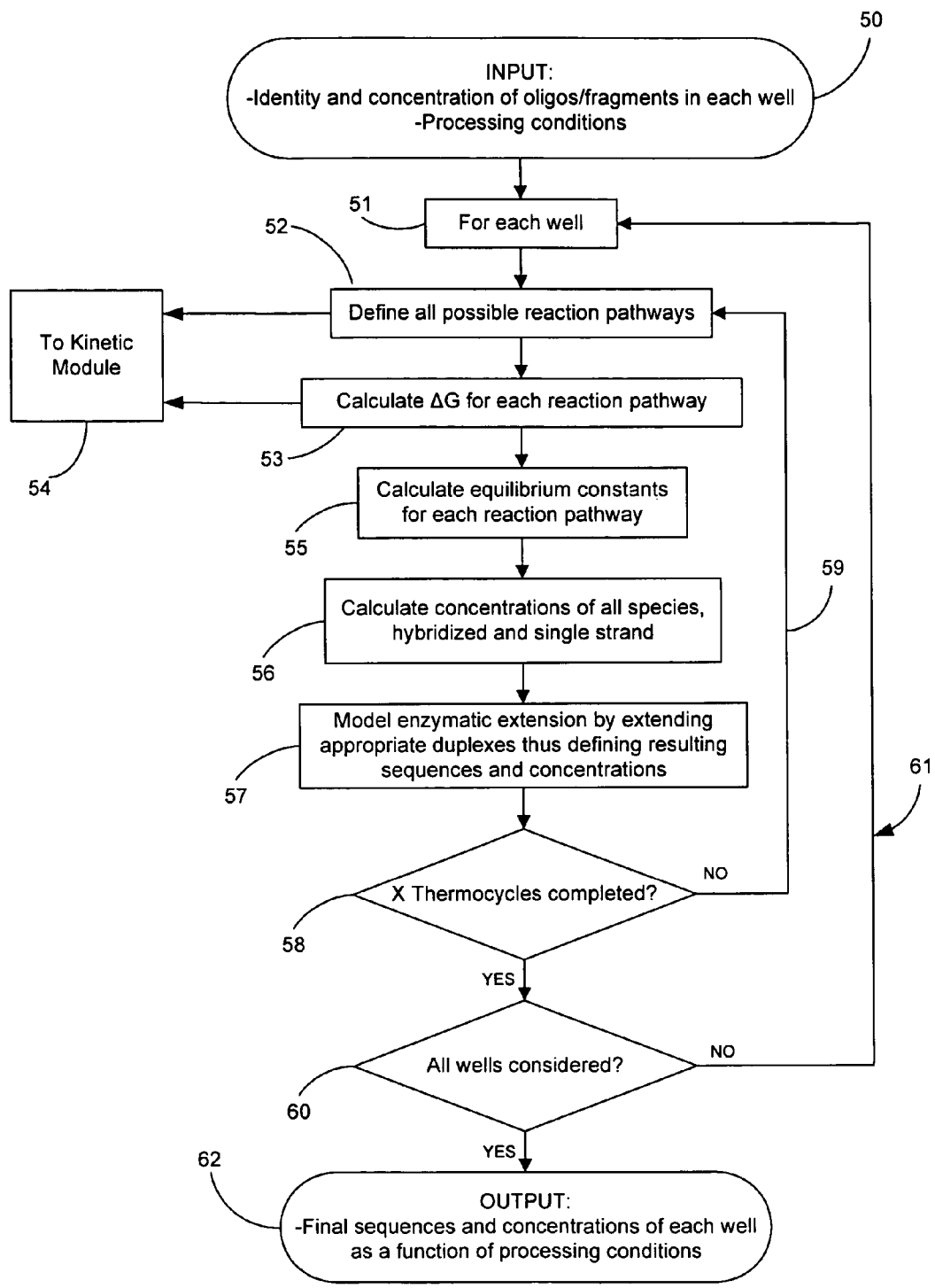
FIG. 4 is a flow diagram of an exemplary thermodynamics module of the present invention.

FIG. 4 shows a flow diagram of the thermodynamics module, having as inputs: the identity and concentration of oligos/fragments in each well, and the processing conditions (i.e. temperature, contaminants, etc.), indicated at 50. Starting at box 51 for each well, all possible reaction pathways are defined at box 52. These reaction pathway definitions are shared with the kinetics module, as indicated at box 54. Next at step 53, the free energy, $\Delta G$, is calculated for each reaction pathway, with the results also shared with the kinetic module, as indicated again at box 54. At step 55, equilibrium constants are calculated for each reaction pathway, and concentrations of all species, hybridized and single strand, are calculated at step 56. Then at 57, enzymatic extension is modeled by extending appropriate duplexes, as known in the art, thus defining resulting sequences and concentrations. The process from step 52 to step 57 is repeated for a predetermined number (X) of thermocycles, as indicated by arrow 59, as determined at step 58. Additionally, the entire process beginning at step 51 is repeated for all wells, as indicated by arrow 61, as determined at step 60. The output 62 from the thermodynamics module include the final sequences and concentrations of each well as a function of processing conditions, and is forwarded to the bioinformatics and kinetic modules.

Kinetic Module

Figure 5:
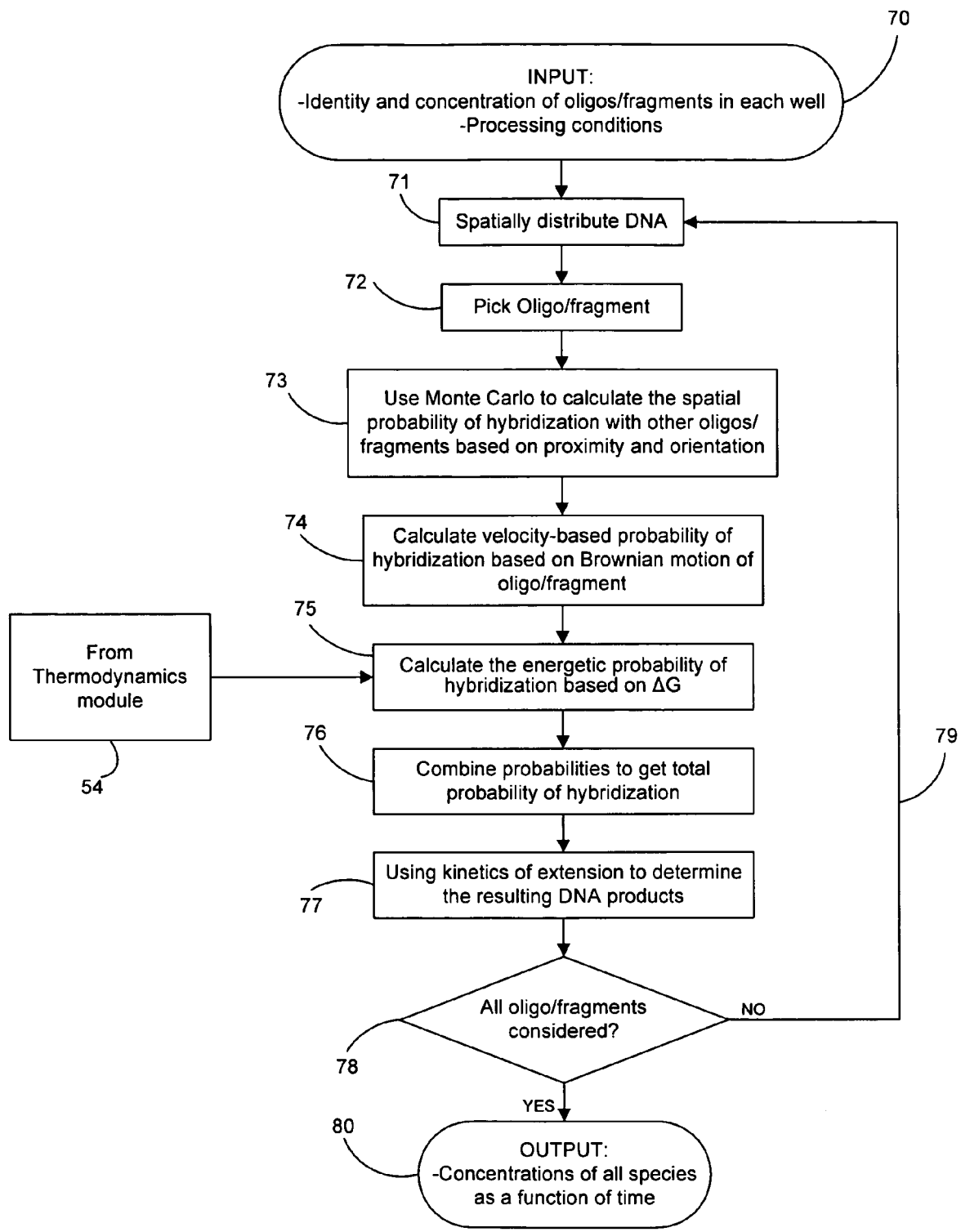
FIG. 5 is a flow diagram of an exemplary kinetic module of the present invention.

FIG. 5 shows a flow chart of the kinetics module, which tracks the temporal and spatial evolution of DNA hybridization and polymerization for all significant reaction pathways that arise during PCR using Stochastic Kinetics [Gillespie, 1976], incorporated by reference herein. Given the initial spatial distribution of the DNA fragments, the kinetic module tracks the system's evolution by examining the probability of a particular reaction as a function of the reaction rate probability of anealing and zippering for perfectly matched oligomers, the base-pair-specific thermodynamic free energies of each pathway and oligomer (primer or probe) proximities, and relative orientations including oligomer mobilities.

Input for the kinetic module is provided at 70 in the form of the identity and concentration of oligos/fragments in each well, and processing conditions, e.g. temperature. At step 71, the DNA is spatially distributed, from which oligos are selected at 72. To determine rates of reaction as a function of proximity, a Monte Carlo simulation is used at 73 to predict the probability of pairs of oligomers being in the proper position to anneal, which takes into account all possible reaction pathways, the concentration of starting oligomers, and the reaction volume. Specifically, the Monte Carlo simulation is used to calculate the spatial probability of hybridization with other oligos/fragments based on proximity and orientation. Next at 74, a calculation is performed to modify the probability of reaction based proximity to account for the Brownian motion of each oligo/fragment. At step 75, the free energy calculation from the thermodynamics module is used, as indicated at 54, to calculate the energetic probability of hybridization that ranges between (0,1] based on the free energy. All the probabilities are then combined with the reaction rate probability for perfect matching at 76 to get the total probability rate of hybridization. Then at 77, kinetics of extension (parameters provided in the literature and known in the art) are used to determine the resulting DNA products. The process beginning at step 71 is repeated for all oligo/fragments as indicated by arrow 79, as determined at 78. Output of the kinetic module includes concentration information of all species, including hybridized and single-strand, as a function of time and processing conditions, e.g., soak times and ramp-rates.

Contaminants

The thermodynamic and kinetic modules of the present invention can also be modified to include modeling of contaminants, e.g. inhibitors, in the PCR reaction. The presence of contaminants may interfere with a PCR reaction, slowing or preventing the process of annealing or enzymatic extension. This problem is of particular concern in DNA-based detection applications, in which environmental samples are tested for the presence of a given pathogen. Extraneous chemicals in the sample may result in false negatives if those chemicals slow the PCR reaction. To address this problem, the effects of contaminants on the thermodynamics and kinetics of the PCR process are examined by and modeled in both the kinetic and thermodynamic modules.

In simulating the process of DNA hybridization, contaminant concentrations and locations are accounted for in the Monte Carlo step 73 of FIG. 5, used in the kinetics module. More specifically, the Monte Carlo step uses the initial concentration and reaction volume to randomly place oligos in the reaction volume. Each reacting pair is compared spatially with all possible partners in the various reaction pathways. The number of oligos of a given sequence that are in proximity is divided by the number of all possible pairs of oligos to predict a probability of reaction for the given pair based on proximity. The same approach is used to randomly place contaminant species in the reaction volume. If a contaminant species physically separates two reacting oligos, this constitutes a blocked reaction and reduces the count of oligos in proximity and results in a reduced probability of reaction for that particular reaction pathway.

The thermodynamic module will account for the presence of contaminants using new thermodynamic hybridization parameters which reflect the presence of the contaminant. In particular, new thermodynamic hybridization parameter are used which are based on experimentally quantification of the effect of the contaminant on the hybridization process, i.e. does the contaminant act as an electrostatic screener and/or a steric blocker? These effects can be quantified through DNA melting experiments in the presence of the contaminant and the thermodynamic parameters altered as deemed necessary. These new parameters will then be used in the thermodynamic module to predict the product distributions in the presence of the contaminant.

Exemplary Applications

The identity of the sequence and concentration of all PCR amplification products determined by the present invention may be utilized for a variety of applications. A first exemplary application involves optimizing conditions for standard PCR reactions. Bioscientists would like to know how modifying variables such as time, temperature, concentration and number of thermocycles could affect the final PCR product. Currently, standard protocols are determined through a limited number of experiments, and slight deviations may yield vastly different results. The method and system of the present invention can provide guidance regarding these protocols.

A second exemplary application of the present invention is the design of artificial gene synthesis protocols utilizing the parallel pyramid approach. While long genes have been assembled by combining many 40-base oligos with DNA polymerase in a single assembly reaction, the ability to synthesize gene starting with short oligos, i.e. less than 10 base pairs, requires the parallel pyramid approach to minimize errors in the assembly process. In this approach, multiple polymerase extension reactions are run in parallel using the initial short DNA. The products of these reactions are then mixed and PCR extension conducted to give longer and longer DNA products. The products of subsequent parallel reactions are mixed in a pyramid manner until the final desired gene product is achieved. The tools provided by the method and system of the present invention enable both the design of the process and the prediction/optimization of the final products.

A third exemplary application of the present invention is in designing microarray chips and in interpreting the data they generate. Analyses of microarray data using, for example, GENECHIPS, microarrays commercially available from Affymetrix, Inc., reveal that in 30% of cases on any one chip, more hybridization occurs with mismatched probe sequences than with their perfectly matching counterpart sequences. This poses a dilemma for interpretation since it is unclear why so many mismatched hybridizations occur with higher affinity than perfect matches. The computational simulation of this problem using the present invention can provide insights to design tools for optimizing probe selection and for minimizing sequences in which mismatch affinities approach those of perfect matches. And data analysis tools could be augmented by probe-specific correction factors accounting for the relative affinities of perfect match and mismatch probes.

A fourth exemplary application of the present invention is in computational pathogen signature development, with virtual PCR utilized as a database tool for pathogen signature selection. Bioinformatics are used to select candidate Taq-Man® signatures for validation in the laboratory. These signatures must be carefully developed to ensure that they are uniquely species-specific to preclude false positives, and that they are species-wide to prevent false negatives due to strain variation. Even with constraints of conservation and uniqueness, for some bacterial genomes the number of possible signature candidates is enormous. To this end, virtual PCR may be utilized to check a given oligomer against a database of all microbial genomes (over 900 Mb) to improve computational pathogen signature selection and to aid pathogen microarray (bug detection chip) design. Further computational elimination of signatures likely to give false positive or negative results is needed so that only the best signatures need to go through expensive laboratory screening. For example, for one 5 Mb pathogen, computational methods have generated 4,000 candidates. A random selection of 400 of those for laboratory screening, yield only a small fraction of which were successful. Sequences that are similar to the target, but that have some mismatches, can be run through virtual PCR simulations and evaluated for their specificity to the target (to prevent false positives), and for their ability to pick up genetic divergence among strains of the target (to avoid false negatives). Strain divergence may be particularly important in cases where a single conserved pair of primer sequences does not exist for divergent, rapidly mutating viruses, and the probability of false negatives must be evaluated. Thus the method and system of the present invention can provide a better computational method to guide, for example, the selection from the 4000 candidates. Computationally predicting specificity to target will be essential as new sequence becomes available. Previously generated and screened signatures must be assessed against new data, and pulled from field use if the likelihood of cross-reaction with non-target is too high. In this manner, virtual PCR can enable experimental efforts to focus from the very start on the best signatures.

And a fifth exemplary application of the present invention is in simulating random amplification. Often for microarray or forensic methods, sample DNA/RNA is present in very low concentrations, and random amplification must be employed prior to analysis. Using the method and system of the present invention described herein, simulations are performed to determine whether the products of random amplification are non-biased. The approach described herein will facilitate the selection of "random" primers to ensure that the amplification is unbiased and will guide the experimental protocol (e.g. time and temperature within and between thermocycles). Forensic assays, for example, Random Amplified Polymorphic DNA (RAPD's) and Amplified Fragment Length Polymorphisms (AFLP's) are related techniques that could also be simulated and optimized from the approach described herein.

While the foregoing invention has been described in some detail for purposes of clarity and understanding, such description is not intended to be limiting. Modifications and changes may become apparent to those skilled in the art without departing from the true scope of the invention in the appended claims.

We claim:

1. A method implemented by a computer system for computationally modeling DNA synthesis, the method comprising:

in a bioinformatics module of the computer system: receiving a desired full-length DNA sequence and a length of starting oligos; using said desired full-length DNA sequence and a first pre-defined set of sequence-based rules to determine optimal starting oligos and well allocations of said optimal starting oligos capable of reducing the production of undesired product; and using a second pre-defined set of sequence-based rules to determine an optimal protocol for mixing the products of a first thermocycle into wells for subsequent thermocycles;

in a thermodynamics module of the computer system: using said optimal starting oligos and well allocations determined in said bioinformatics module to track all possible reaction pathways that arise during each thermocycle and hybridization in terms of equilibrium thermodynamics by determining, for a given mix of DNA, the probability of hybridization for all the possible combinations of oligos as determined by the free energies of interaction, wherein the concentrations of all species of single and hybridized sequences in each well are determined as a function of processing conditions; extending all hybridized strands which can be biologically extended by the polymerase; and using all sequences and concentrations in a thermocycle as input for a subsequent thermocycle;

in a kinetic module of the computer system, using said optimal starting oligos and well allocations determined in said bioinformatics module and said concentrations of all species determined in said thermodynamics module to track temporal and spatial evolution of hybridization and polymerization for all of said possible reaction pathways that arise during thermocycling and hybridization, by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions;

from an output module of the computer system: outputting predicted synthesis products information to a user based on outputs of said thermodynamic module and said kinetic module.

2. The method of claim 1, wherein, in said bioinformatics module, said first and second pre-defined sets of sequence-based rules are based on an error determination due to at least one of: length of starting fragments; melting temperatures, self-complementarity of fragments, incorrect but perfectly matching hybridizations, mismatched fragments that nevertheless have high melting temperatures, fragment sequences that are difficult to synthesize, and overlap between wells.

3. The method of claim 2, wherein said error determination includes determining whether the addition of a next oligo creates an error so as to define the synthesized length for a defined reading frame.

4. The method of claim 3, wherein a reading frame which produces the maximum amount of DNA is chosen and defined as an optimal well.

5. The method of claim 1, wherein, in the thermodynamics module, said processing conditions include temperature, thermocycle and concentration, as well as the fragment identity and mixture determined in said bioinformatics module.

6. The method of claim 1, wherein the parameters used in the thermodynamics module for tracking and determination are nearest neighbor parameters for DNA melting and the probabilities of polymerase extensions as a function of base pair mismatches.

7. The method of claim 1, further comprising, in the kinetic module, using a Monte Carlo simulation to predict the probability of pairs of oligomers being in the proper position to anneal which takes into account all possible reaction pathways, the concentration of starting oligomers, and the reaction volume.

8. The method of claim 1, further comprising checking a given oligomer against a database of microbial genomes.

9. A computer system for computationally modeling DNA synthesis, the computer system comprising:

a bioinformatic module adapted to receive a desired full-length DNA sequence and a length of starting oligos; use said desired full-length DNA sequence and a first pre-defined set of sequence-based rules to determine optimal starting oligos and well allocations of said optimal starting oligos capable of reducing the production of undesired product; and use a second pre-defined set of sequence-based rules to determine an optimal protocol for mixing the products of a first thermocycle into wells for subsequent thermocycles;

a thermodynamics module adapted to use said optimal starting oligos and well allocations determined in said bioinformatics module to track all possible reaction pathways that arise during each thermocycle and hybridization in terms of equilibrium thermodynamics by determining, for a given mix of DNA, the probability of hybridization for all the possible combinations of oligos as determined by the free energies of interaction, wherein the concentrations of all species of single and hybridized sequences in each well are determined as a function of processing conditions; extended all hybridized strands which can be biologically extended by the polymerase; and use all sequences and concentrations in a thermocycle as input for a subsequent thermocycle;

a kinetic module adapted to use said optimal starting oligos and well allocations determined in said bioinformatics module and said concentrations of all species determined in said thermodynamics module to track temporal and spatial evolution of hybridization and polymerization for all of said possible reaction pathways that arise during thermocycling and hybridization and determine concentrations of all species, by examining the probabilistic rate reaction of a particular reaction as a function of the probability rate for perfect matching attenuated by the probabilities based on the base-pair-specific thermodynamic free energies and oligomer proximities, relative orientations, mobilities and processing conditions; and an output module for outputting predicted synthesis products to a user based on outputs of said thermodynamic module and said kinetic module.

* * * * *